United States Patent
Rubin et al.

(10) Patent No.: US 6,303,660 B1
(45) Date of Patent: Oct. 16, 2001

(54) ENHANCED ANTI-CANCER AGENT DELIVERY TO SOLID TUMORS BY PRIMER COMPOUNDS

(75) Inventors: Kristofer Rubin; Mats Sjoquist, both of Uppsala (SE); Rolf Reed, Bergen (NO)

(73) Assignee: Biophausia AB (publ), Uppsala (SE)

( * ) Notice: Subject to any disclaimer, the term of this patent is extended or adjusted under 35 U.S.C. 154(b) by 0 days.

(21) Appl. No.: 09/424,256

(22) PCT Filed: May 26, 1998

(86) PCT No.: PCT/EP98/03078

§ 371 Date: Feb. 1, 2000

§ 102(e) Date: Feb. 1, 2000

(87) PCT Pub. No.: WO98/55112

PCT Pub. Date: Dec. 10, 1998

(30) Foreign Application Priority Data

Jun. 2, 1997 (SE) .................................................. 9702086

(51) Int. Cl.[7] .......................... A61K 47/14; A61K 31/505
(52) U.S. Cl. .......................... 514/785; 514/724; 514/277; 514/544; 514/313
(58) Field of Search .................................. 514/785, 724, 514/274; 549/313

(56) References Cited

U.S. PATENT DOCUMENTS

| | | | | |
|---|---|---|---|---|
| 4,654,366 | * | 3/1987 | Varma et al. ........................ | 514/469 |
| 4,654,367 | * | 3/1987 | Varma et al. ........................ | 514/469 |
| 4,751,224 | * | 6/1988 | Agarwal .............................. | 514/248 |

OTHER PUBLICATIONS

"Macrophage cytok.render WEHI–3B Tum. Cell. . .", Efraim et al.Prostg. Leuk. & Ess., 40/2, 163–7, Jun. 1990.*
"Local Prostg. E2 in Patient.", Porteder et al. J.Cranio-Maxillo–Fac., 16/8,371–4, Nov. 1988.*
"Neuroblastoma:Incomplete differ. on the way yo maturation of.", Ogita etal. Oncology, 45/3, 148, Jun. 1990.*

H. Koga et al., "Increased delivery of a new cisplatin analogue (254–S) in a rat brain tumor by an intracarotid infusion of bradykinin.", Neurol. Res., 1996, XP002082232.
K.L. Black et al., "Intracarotid infusion of RMP–7, a bradykinin analog, and transport of gallium–68 ethylenediamine tetraacetic acid into human gliomas." J. Neurosurg., 1997, XP002082233.
K. Miyamoto et al., "Enhancement of mitomycin C uptake by isoproterenol in rat ascites hepatoma." J. Pharmaco–Biodyn, 1986, XP002082234.
K. Miyamoto et al.,"Comparative studies on the combined cytotoxic effects of forskolin with mitomycin C and responsiveness to forskolin in rat ascites heptamona AH66 cells and AH66F cells." J. Pharmaco–Biodyn, 1987, XP002082235.
N. Shinomiya et al., "Enhancement of CDDP cytotoxicity by caffeine is characterized by apoptotic cell death.", Exp. Cel Res., 1994, XP002082236.
D.R. Shalinsky et al., "Selective modulation of vinblastine sensitivity by 1,9–dideoxyforskolin and related diterpenes in multidrug resistant tumor cells." BR. J. Cancer, 1993, XP002082237.
H.J. Fingert et al., "In vivo and in vitro enhanced antitumor effects by pentoxifylline in human cancer cells treated by thiotepa.", Cancer Res., 1988, XP002082238.

* cited by examiner

Primary Examiner—Richard L. Raymond
Assistant Examiner—Sudhaker B. Patel
(74) Attorney, Agent, or Firm—Bacon & Thomas

(57) ABSTRACT

Primer compositions for anti-cancer agent delivery to solid tumors in mammals, including man, are disclosed. The primer comprise a pharmaceutically acceptable agent which increases the intracellular levels of cyclic adenosine monophosphate (cAMP) in the normal connective tissue cells within solid tumors. Such an agent may be selected from any agents which increase the intracellular levels of cAMP, e.g. agents binding to and stimulating receptors at the connective tissue cell surface within tumors, and agents inhibiting cAMP phosphodiesterase. Local administration of the primer to the solid tumor area results in a lowering of the interstitial pressure. Further, an agent delivery system and a method for delivery of anti-cancer agents to solid tumors are described.

16 Claims, No Drawings

ENHANCED ANTI-CANCER AGENT DELIVERY TO SOLID TUMORS BY PRIMER COMPOUNDS

The present invention relates to a new approach to deliver anti-cancer agents to solid malignant tumors. Specifically, it relates to a primer composition for local delivery to primary solid malignant tumors or metastases thereof in mammals, including man, prior to administration of anti-cancer agents. Further, it relates to an agent delivery system and a method of delivering an anti-cancer agent to primary solid malignant tumors and metastases thereof.

BACKGROUND

Anti-cancer agents are often administered orally or by injection for transportation by the blood stream to the solid tumors in the liver, lung, breast, colon, rectum, prostate or brain. The anti-cancer agent must be transported by blood to the blood vessels of the tumor, pass the vessel wall, and go through the interstitium to reach the cancer cell. Unfortunately, in many cases, the agents are not as efficient as expected from results of toxicity tests with cultured malignant cancer cells. This is probably due to barriers to agent delivery in solid tumors (R. K. Jain, Sci. Am. 271 (1994) 58). Thus, there is a need for improvement in anti-cancer agent delivery to solid tumors.

Solid malignant tumors comprise normal connective tissue cells in addition to malignant cancer cells within the tumor. The malignant cancer cells occupy only a part of the volume of the tumor and they are surrounded by the interstitium, i. e. a collagen rich extracellular matrix which can separate the cancer cells from the unevenly distributed blood vessels, which constitute approximately 1–10% of the tumor.

Rakesh K. Jain (ibid.) recognized inter alia that the abnormally high pressure in the interstitial matrix of a solid tumor can retard the passage of large molecules across vessel walls into the interstitial matrix and thus contribute to a low concentration of agent molecules frequently seen in the interstitial matrix of animal and human tumors growing in mice. He suggested among other things two pressure-related strategies to improve solid tumor therapy, namely injection of an agent mixed with a large amount of fluid directly into the center of a tumor to increase the pressure at the core of the tumor relative to the surrounding tumor tissue so that the agent would spread along the induced pressure gradient, and reduction of the interstitial pressure with the vasodilators pentoxifylline or high, near toxic doses, of the vitamin B3 derivative nicotinamide. Both agents are known to increase the oxygen supply in various tumors which is a benefit for radiation therapy.

DESCRIPTION OF THE INVENTION

The present invention is concerned with means and methods to improve anti-cancer agent delivery to solid malignant tumors in mammals, including man.

Particularly, the invention provides a new approach to anti-cancer agent delivery to primary solid malignant tumors or metastases thereof in that a primer composition is administered locally to lower the interstitial pressure in the solid tumor area, which facilitates the subsequent transport of locally or systemically administered anti-cancer agents to the solid tumors.

Specifically, the present invention is directed to a primer composition for local delivery to primary solid malignant tumors or metastases thereof in mammals, including man, prior to administration of anti-cancer agents, comprising an interstitial pressure-lowering amount of a pharmaceutically acceptable agent which increases the intracellular levels of cyclic adenosine monophosphate (cAMP) in the normal connective tissue cells within the solid malignant tumors, and a vehicle.

Such an agent may be selected from any agents which increase the intracellular levels of CAMP, such as agents that bind to and stimulate receptors at the cell surface of normal connective tissue cells within the tumor, and agents that inhibit CAMP phosphodiesterase.

Specific examples of agents known to bind to and stimulate receptors that increase intracellular levels of cAMP are Bradykinin, Histamine, Vasoactive intestinal polypeptide (VIP), Isoproterenol, Forskolin, and Prostaglandin $E_1$, Prostaglandin $E_2$, Prostaglandin $I_2$ and esters of these prostaglandins.

Further, examples of esters of the prostaglandins are Prostaglandin $E_1$ methyl ester, Prostaglandin $E_1$ ethyl ester, Prostaglandin $E_1$ isopropyl ester and 6a-Carba-prostaglandin $I_2$ (Carbacyclin).

Examples of agents known to inhibit cAMP phosphodiesterase are 3-Isobutyl methyl xanthine,Theophylline, Rolipram, Motapizone, Caffeine and Zardarverine.

It should be understood that the pharmaceutically acceptable agent, which increases the intracellular levels of cyclic adenosine monophosphate (cAMP) in normal connective tissue cells within solid malignant tumors, in the primer composition of the present invention, is not limited to the above exemplified agents and that any pharmaceutically acceptable agent which increases the intracellular levels of cyclic adenosine monophosphate (cAMP) in the normal connective tissue cells within solid malignant tumors is comprised by the scope of the invention.

Further, local administration or delivery of the primer composition of the invention is intended to comprise installing or injection to the surroundings of the tumor(s) such as the immediate surrounding tissue or blood vessel supporting the tumor-containing organ, e g via a cannula.

The vehicle of the primer composition according to the invention may be any pharmaceutically acceptable vehicle which is suitable for local delivery of the primer composition of the invention, such as isotonic saline solution, phosphate buffered saline (PBS) solution, ethanol etc.

The interstitial pressure-lowering amount of the agent will be determined empirically for each specific agent which increases the intracellular levels of cAMP, but the amount will normally be in the range of 1 to 10 mg per kg body weight.

The present invention is further directed to an agent delivery system for delivery of anti-cancer agents to primary solid malignant tumors or metastases thereof in mammals, including man. The system comprises as a first component,
  a) a primer composition according to any one of claims 1–3 for initial local delivery to a solid tumor area, and as a second component,
  b) a therapeutically effective amount of an anti-cancer agent for subsequent local or systemic administration.

In case a specific anti-cancer agent needs an adjuvant for improved uptake, the delivery system of the invention may comprise such an adjuvant.

The present invention is also directed to a method of delivering an anti-cancer agent to primary solid malignant tumors or metastases thereof in mammals, including man. The method comprises the steps of a first local administration to the tumor area of a primer composition comprising
  an interstitial pressure-lowering amount of a pharmaceutically acceptable agent which increases the intracellular levels of cyclic adenosine monophosphate (cAMP) in the normal connective tissue cells within solid tumors, and a vehicle,
to effect lowering of the interstitial pressure, followed by
    a second local or systemic administration of a therapeutically effective amount of an anti-cancer agent.

The therapeutically effective amount of a specific anti-cancer agent will be determined on the basis of the amount recommended by the manufacturer.

It should be understood that in the present specification and claims the primer composition is administered locally to the tumor area prior to the delivery of an anti-cancer agent so that the interstitial pressure-lowering effect of the primer composition is sufficient to facilitate the transport of the anti-cancer agent to the cancer cells of the solid tumor.

The time interval between the administration of the primer composition and the anti-cancer agent will depend on several patient-related factors and the actual composition and agent. However, from less than a minute to up to a few hours may be used, even though the interval normally will be between 3 minutes and 2 hours, e.g. 5 to 60 minutes, such as 10 to 50 minutes.

The invention is further illustrated by the following experiments, which should not be considered to limit the scope of the invention.

EXPERIMENTS
Experimental Subcutaneous Tumors in Rats $5 \times 10^6$ PRO b tumor cells (Int. J. Cancer 65, 796–804 (1996)) in PBS were injected subcutaneously below the left shoulder on male or female BD IX (syngeneic) rats (weighing 200–400 g) (from Charles River, Germany).

Tumor growth was monitored and after approximately 2 months a tumor of an average weight of 2 g had appeared (external—on the skin—sizes between 0.5–2 cm in diameter). Experiments were conducted at various tumor sizes.

Animals were anesthetized with Inactin (sodium 5-sec-butyl-5-ethyl-2-thiobarbiturate; Byk-Gulden, Konstanz, Germany) given intraperitoneally in a dose of 120 mg kg$^{-1}$ BW (=body weight).

Animals were placed on a servo-controlled heating pad to maintain the rectal temperature at 37.5° C.

After tracheotomy the left femoral vein was cannulated for continuous infusion (mL h$^{-1}$ kg$^{-1}$ BW) of Ringer solution (129 mm NaCl, 2.5 mm KCl, 25 mm NaHCO$_2$, 0.75 mM CaCl$_2$), which was given to compensate for fluid losses during the experiment. The left femoral artery was cannulated to continuously measure blood pressure. Tumor interstitial fluid pressure was monitored continuously through a 23G needle modified according to a "wick-in-the needle" (H. O. Fadnes, et al, Microvascular Research, Vol 14, 27–36 (1977)), inserted into the tumor.

When blood and tumor interstitial fluid pressure had stabilized, the agent (15 μg of PGE$_1$ methyl ester (Sigma P439)) in PBS with approximately 3% Ethanol (20 μl of PGE$_1$ methyl ester, 313 μL of 70% ethanol, 6.33 mL of PBS) was installed locally around the tumor (injected as 4 or 5 doses).

Control: 1 mL of vehicle (333 μL ethanol, 6.33 mL PBS) was installed locally around the tumor (injected as 4 or 5 doses).

RESULTS

A total of 14 tumor-bearing rats were investigated in the present series. To 7 of these vehicle was administrated around the tumors, and pressures were recorded (Table 1). When the blood and tumor interstitial fluid pressures had stabilized, 40 nmol of Prostaglandin E$_1$ methyl ester was installed around the tumors, and the pressures were recorded.

TABLE I

Effects of local administration of vehicle around subcutaneous tumors.

| Time | Tumor Interstitial Fluid Pressure mmHg (n/ ± SD/ ranges) | Blood Pressure mmHg (n/ ± SD/ ranges) |
|---|---|---|
| 0 (start) | 15.7 (7/ ± 6.98/9.50–29.0) | 119 (7/ ± 14.4/98.0–143) |
| 5 min | 15.9 (7/ ± 6.38/10.50–28.0) | 117 (7/ ± 12.4/98.0–139) |

In 7 rats, 40 nmol of Prostaglandin E$_1$ methyl ester was installed directly and not after a first administration of vehicle(Table II).

TABLE II

Effects of local administration of 40 nmol Prostaglandin E$_1$ methyl ester around subcutaneous tumors. Time course.

| Time | Tumor Interstitial Fluid Pressure mmHg (n/ ± SD/ ranges) | Blood Pressure mmHg (n/ ± SD/ ranges) |
|---|---|---|
| 0 (start) | 16.7 (14/ ± 5.77/9.30–30.0) | 120 (14/ ± 9.70/103–134) |
| 1 min | 13.9 (14/ ± 5.49/5.00–26.5) | 96.9 (14/ ± 15.2/68.0–144) |
| 5 min | 12.1 (13/ ± 4.937 4.00–22.0) | 94.8 (13/ ± 14.3/61.0–113) |
| 10 min | 11.3 (13/ ± 4.317 3.00–16.5) | 96.6 (13/ ± 14.1/62.0–114) |
| 20 min | 11.0 (9/ ± 4.16/4.00–17.0) | 99.2 (9/ ± 12.1/81.9–114) |
| 30 min | 9.80 (5/ ± 4.21/4.00–14.0) | 98.6 (5/ ± 9.63/88.0–111) |
| 40 min | 9.53 (4/ ± 4.91/4.00–14.0) | 102 (4/ ± 8.66/91.9–112) |

TABLE III

Pressure in individual tumors after administration of 40 nmol Prostaglandin E$_1$ methyl ester around subcutaneous tumors.

| Rat Identification[a] | Rat Weight (g) | Tumor Weight (g) | Tumor Interstitial Fluid Pressure (mm Hg) | | | Blood Pressure (mm Hg) | | |
|---|---|---|---|---|---|---|---|---|
| | | | Start | 10'[b] | % Change | Start | 10' | % Change |
| #1 (male) | 380 | 8.5 | 21 | 15 | −29 | 125 | 109 | −13 |
| #2 (male) | 460 | 2.5 | 23 | 16 | −30 | 134 | 114 | −15 |
| #3 (male) | 448 | 1.6 | 18 | 16 | −11 | 126 | 102 | −19 |
| #4 (male) | 380 | ~1 | 21 | 3 | −86 | 112 | 102 | −9 |

TABLE III-continued

Pressure in individual tumors after administration of 40 nmol Prostaglandin $E_1$ methyl ester around subcutaneous tumors.

| Rat Identification[a] | Rat Weight (g) | Tumor Weight (g) | Tumor Interstitial Fluid Pressure (mm Hg) | | | Blood Pressure (mm Hg) | | |
|---|---|---|---|---|---|---|---|---|
| | | | Start | 10'[b] | % Change | Start | 10' | % Change |
| #5 (male)    | 246 | 4.3 | 10.5 | 7    | −33 | 123 | 101 | −18 |
| #6 (male)    | 324 | ~1  | 11.5 | 7.5  | −35 | 103 | 93  | −7  |
| #7 (male)    | 350 | 1.9 | 12.5 | 9.5  | −24 | 114 | 99  | −14 |
| #8 (male)    | 313 | 3.6 | 30   | 16.5 | −45 | 131 | 95  | −27 |
| #9 (male)    | 347 | 5.6 | 18.5 | 13.5 | −27 | 108 | 88  | −18 |
| #10 (female) | 192 | 3.6 | 18.5 | 14.5 | −22 | 120 | 103 | −14 |
| #11 (female) | 181 | 1.8 | 13   | 11.5 | −12 | 115 | 78  | −32 |
| #12 (female) | 188 | 1.0 | 9.3  | 7.5  | −19 | 127 | 110 | −13 |
| #13 (female) | 217 | 1.4 | 14.5 | 9.8  | −32 | 125 | 102 | −18 |

Table III (cont.)
  Blood Pressure % Change: −16.7±6.8 p<0.001 (n=13)
  Tumor Interstitial Fluid Pressure % Change: −31.2±5.3 p<0.001 (n=13)

(a) One rat of the 14 included in this experimental series had to be excluded from this table since no relevant recording was obtained 10 minutes after installment of 40 nmol prostaglandin $E_1$-methyl ester.
  (b) Denotes 10 minutes after installment of 40 nmol prostaglandin $E_1$-methyl ester.
  % Change Denotes percent of start value at 10 minutes after installment of 40 nmol prostaglandin $E_1$-methyl ester (±SD).

TABLE IV

Pressure in individual tumors after administration of 40 nmol vehicle around subcutaneous tumors.

| Rat Identification | Rat Weight (g) | Tumor Weight (g) | Tumor Interstitial Fluid Pressure (mm Hg) | | | Blood Pressure (mm Hg) | | |
|---|---|---|---|---|---|---|---|---|
| | | | Start | 5'[a] | % Change | Start | 5' | % Change |
| #5 (male)    | 246 | 4.3 | 9.5  | 10.5 | +11 | 125 | 123 | −2 |
| #6 (male)    | 324 | ~1  | 10.5 | 11   | +5  | 98  | 98  | 0  |
| #7 (male)    | 350 | 1.9 | 12   | 12.5 | +6  | 114 | 114 | 0  |
| #8 (male)    | 313 | 3.6 | 29   | 28   | −3  | 143 | 138 | −3 |
| #9 (male)    | 347 | 5.6 | 19   | 18.5 | −3  | 107 | 109 | +2 |
| #10 (female) | 194 | 3.6 | 18.5 | 18.5 | 0   | 123 | 120 | −2 |
| #11 (female) | 181 | 1.8 | 11.5 | 11.5 | 0   | 121 | 115 | −5 |

Table IV (cont.)
  Blood Pressure % Change: −1.4±2.3 p>0.05 ns
  Tumor Interstitial Fluid Pressure % Change: +2.3±5.2 p>0.05 ns
  (a) Denotes 5 minutes after installment of vehicle.
  % Change Denotes percent of start value at 5 minutes after installment of vehicle (±SD). ns=not significant Experimental Mammary Tumors in Rats Dimethyl benzanthracene (DMBA)-induced mammary tumors in rats (Wistar, Möllegaard, Denmark). One administration of DMBA, 16 mg in olive oil, intra gastrically. Tumors developed during the subsequent 7 weeks.

Animals were anaesthetized with sodium phenobarbital 50 mg kg$^{-1}$ given intraperitoneally.

Animals were placed on a servo-controlled heating pad which maintained the rectal temperature at 37.5° C.

The left femoral artery was cannulated to continuously measure blood pressure. Tumor interstitial fluid pressure was monitored continuously through a 23G needle modified according to a "wick-in-the needle", inserted into the tumor.

When tumor interstitial fluid pressure had stabilized 1 ml of the agent (15 μg of $PGE_1$, methyl ester (Sigma P439)) in PBS with approximately 3% Ethanol (20 μL $PGE_1$, methyl ester, 313 μL 70% ethanol, 6.33 mL PBS) was installed locally around the tumor (injected as 4 or 5 doses).

Control: 1 mL of (333 μL ethanol, 6.33 mL PBS) was installed locally around the tumor (injected as 4 or 5 doses).

RESULTS

TABLE V

Effects of local administration of vehicle around mammary tumors.

| | Tumor interstitial fluid pressure (mmHg) | | |
|---|---|---|---|
| Tumor weight (g) | initial | After NaCl | % Change |
| 1.29 | 5.0 | 6.5 | +30 |
| 1.20 | 6.0 | 6.0 | 0 |
| 1.78 | 6.0 | 7.0 | +17 |
| 2.19 | 3.0 | 3.0 | 0 |
| 2.35 | 4.0 | 4.3 | +7.5 |
| 1.36 | 3.3 | 3.3 | 0 |
| Mean ± SD | 4.6 ± 1.3 | 5.0 ± 1.7 | +9.1 ± 12.2 |
| (n = 6) | | | p > 0.05 ns |

TABLE VI

Effects of local administration of 40 nmol Prostaglandin $E_1$ methyl ester around mammary tumors (tumors with interstitial fluid pressure below 9 mmHg).

| | Tumor interstitial fluid pressure (mmHg) | | |
|---|---|---|---|
| | | After local administration of prostaglandin $E_1$ methyl ester | |
| Tumor weight (g) | Initial | | % Change |
| 1.35 | 5.0 | 2.5 | −50 |
| 2.25 | 7.0 | 5.0 | −29 |
| 0.90 | 5.0 | 3.0 | −40 |
| 2.65 | 7.0 | 6.5 | −7.1 |
| 3.54 | 4.5 | 4.0 | −11 |
| 3.15 | 6.5 | 4.0 | −23 |
| Mean ± SD | 5.8 ± 1.1 | 4.2 ± 1.4 | −26.7 ± 16.6 |
| (n = 6) | | | p < 0.02 |

TABLE VII

Effects of local administration of 40 nmol Prostaglandin $E_1$ methyl ester around mammary tumors (tumors with interstitial fluid pressure above 9 mmHg).

| | Tumor interstitial fluid pressure (mmHg) | | |
|---|---|---|---|
| | | After local administration of prostaglandin $E_1$ methyl ester | |
| Tumor weight (g) | Initial | | % Change |
| 3.92 | 9.0 | 7.0 | −22.2 |
| 3.49 | 12.0 | 10.5 | −12.5 |
| 3.54 | 17.0 | 11.0 | −35.3 |
| 3.15 | 10.0 | 8.0 | −20 |
| Mean ± SD | 12.0 | 9.1 | −22.5 ± 9.5 |
| (n = 4) | | | p < 0.05 |
| Mean ± SD | 8.3 ± 3.9 | 6.2±3.0 | −25.0 ± 13.7 |
| (n = 10) | | | p < 0.02 |

Local administration of 40 nmol Prostaglandin $E_1$ methyl ester around the mammary tumors led to a significant decrease in interstitial fluid pressure (Tables VI and VII), whereas administration of vehicle alone was without effect (Table V).

RESULTS OF INTERSTITIAL FLUID PRESSURE STUDIES

These results demonstrate that local administration of prostaglandin $E_1$ methyl ester induces a lowering of the interstitial fluid pressure in two different experimental tumors. The decrease in interstitial fluid pressure was in the order of 30% in both tumors, and was not immediately dependent on tumor weight. In the PRO-b cells the relation between the effects of prostaglandin $E_1$ methyl ester on blood pressure and tumor interstitial fluid pressure is clearly demonstrated. The data show that the effects of prostaglandin $E_1$ methyl ester on tumor interstitial fluid pressure were more pronounced and persisted for a longer time period than the effects of this compound on the blood pressure. Therefore, we concluded that effects on blood pressure are not directly related to effects on tumor interstitial fluid pressure.

Microdialysis on Enhanced Uptake in the Tumor $5 \times 10^6$ PRO b tumor cells (Int. J. Cancer 65, 796–804 (1996)) in PBS were injected subcutaneously below the left shoulder on male or female BD IX (syngeneic) rats (weighing 200–400 g) (from Charles River, Germany).

Tumor growth was monitored and after approximately 2 months a tumor of an average weight of 2 g had appeared (external —on the skin —sizes between 0.5–2 cm in diameter). Experiments were conducted at various tumor sizes.

Animals were anesthetized with Inactin (sodium 5-sec-butyl-5-ethyl-2-thiobarbiturate; Byk-Gulden, Konstanz, Germany) given intraperitoneally in a dose of 120 mg $kg^{-1}$ BW (=body weight).

Animals were placed on a servo-controlled heating pad to maintain the rectal temperature at 37.5° C.

After tracheotomy the left femoral vein was cannulated for continuous infusion (5 mL $h^{-1}$ $kg^{-1}$ BW) of Ringer solution (129 mm NaCl, 2.5 mm KCl, 25 mm $NaHCO_2$, 0.75 mM $CaCl_2$), which was given to compensate for fluid losses during the experiment. The left femoral artery was cannulated to continuously measure blood pressure.

A microdialysis probe, CMA/20, (from CMA/Microdialysis AB, Solna, Sweden) was positioned in the central part of the tumor by preforming a hole with a 0.8 mm cannula. The cannula was removed and the probe was inserted. The left femoral vein was exposed and a second microdialysis probe was introduced into the vein. The probes were connected to a microinjection pump with the flow set to 2.5 μl/min to each probe. The dialysate was sterile isotonic saline. Fractions from the probes were collected at 10 min intervals.

When the blood pressure had stabilized 40 nmol of Prostaglandin $E_1$ methyl ester was injected around the tumor in 1 ml vehicle (PBS). In another rat only the vehicle was injected around the tumor. After 40 min, 100 μ$Ci^{51}$Cr-EDTA was injected intravenously.

The rate constant for the diffusion of $^{51}$Cr-EDTA into the tumor compartment was estimated using a simple two compartment model, minimizing the sum of the squared deviations from the experimental values.

Results From the Microdialysis Experiments.

Forty minutes after $PGE_1$ methyl ester injection the rate constant to the tumor compartment was increased by 10%.

This is the result from the first microdialysis experiment conducted at only one time, i.e. forty minutes after $PGE_1$ methyl ester injection, and so the experimental conditions have not been optimized.

What is claimed is:

1. Agent delivery system for delivery of anti-cancer agents to primary solid malignant tumors and metastases thereof in mammals, including man, comprising two components to be administered one after the other with a time interval between the administrations, wherein the first component is,
- a) a primer composition for local delivery to primary solid malignant tumors or metastases thereof in mammals, including man, prior to administration of anti-cancer agents, comprising an interstitial pressure-lowering amount of a pharmaceutically acceptable agent which increases the intracellular levels of cyclic adenosine monophosphate (cAMP) in the normal connective tissue cells within solid malignant tumors selected from the group consisting of Prostaglandin $E_1$, Prostaglandin $E_2$, Prostaglandin $I_2$, and esters of these prostaglandins, and a vehicle, for initial local delivery to a solid tumor area, and the second component is,
- b) a therapeutically effective amount of an anti-cancer agent for subsequent local or systemic administration.

2. Agent delivery system according to claim 1, which further comprises an adjuvant for the anti-cancer agent.

3. Method of delivering an anti-cancer agent to primary solid malignant tumors and metastases thereof in mammals, including man, comprising a first local administration to the tumor area of a primer composition comprising an interstitial pressure-lowering amount of a pharmaceutically acceptable agent which increases the intracellular levels of cyclic adenosine monophosphate (cAMP) in the normal connective tissue cells within solid tumors selected from the group consisting of Prostaglandin $E_1$, Prostaglandin $E_2$, Prostaglandin $I_2$, and esters of these prostaglandins, and a vehicle, to effect lowering of the interstitial pressure, followed after a time interval by a second local or systemic administration of a therapeutically effective amount of an anti-cancer agent.

4. Method of delivering an anti-cancer agent according to claim 3, wherein the esters of the prostaglandins are selected from the group consisting of Prostaglandin $E_1$ methyl ester, Prostaglandin $E_1$ ethyl ester, Prostaglandin $E_1$ isopropyl ester and 6a-Carba-prostaglandin $I_2$ (Carbacyclin).

5. The agent delivery system of claim 1 wherein the esters of the prostaglandins are selected from the group consisting of Prostaglandin $E_1$ methyl ester, Prostaglandin $E_1$ ethyl ester, Prostaglandin $E_1$ isopropyl ester and 6a-Carba-prostaglandin $I_2$ (Carbacyclin).

6. The agent delivery system of claim 1, wherein the pharmaceutically acceptable agent is Prostaglandin $E_1$.

7. The agent delivery system of claim 1, wherein the pharmaceutically acceptable agent is Prostaglandin $E_1$ methyl ester.

8. The agent delivery system of claim 5 which further comprises an adjuvant for the anti-cancer agent.

9. The method of claim 3, wherein the pharmaceutically acceptable agent is Prostaglandin $E_1$.

10. The method of claim 3, wherein the pharmaceutically acceptable agent is Prostaglandin $E_1$ methyl ester.

11. The method of claim 3 which further comprises administering an adjuvant for the anti-cancer agent.

12. A method of delivering the agent according to claim 1, wherein the first component a) is initially locally delivered to a solid tumor area, and the second component, b) is administered in a therapeutically effective amount subsequently and locally or systemically.

13. The method of claim 12, wherein the esters of the prostaglandins are selected from the group consisting of Prostaglandin $E_1$, methyl ester, Prostaglandin $E_1$ ethyl ester, Prostaglandin $E_1$ isopropyl ester and 6a-Carba-prostaglandin $I_2$ (Carbacyclin).

14. The method of claim 12, wherein the pharmaceutically acceptable agent is Prostaglandin $E_1$.

15. The method of claim 12 which further comprises administering an adjuvant for the anti-cancer agent.

16. The method of claim 13, wherein the pharmaceutically acceptable agent is Prostaglandin $E_1$, methyl ester.

* * * * *